United States Patent [19]

Bank

[11] Patent Number: 5,359,113
[45] Date of Patent: Oct. 25, 1994

[54] METHOD FOR MAINTAINING CATALYTIC ACTIVITY DURING A HYDROSILYLATION REACTION

[75] Inventor: Howard M. Bank, Freeland, Mich.

[73] Assignee: Dow Corning Corporation, Midland, Mich.

[21] Appl. No.: 148,944

[22] Filed: Nov. 8, 1993

[51] Int. Cl.$^5$ .............................. C07F 7/08
[52] U.S. Cl. .................................... 556/479
[58] Field of Search ....................... 556/479

[56] References Cited

U.S. PATENT DOCUMENTS

| | | | |
|---|---|---|---|
| 2,823,218 | 2/1958 | Speier et al. | 260/448.2 |
| 3,220,972 | 11/1965 | Lamoreaux | 260/46.5 |
| 4,398,010 | 8/1983 | Adkins | 556/479 X |
| 4,578,497 | 3/1986 | Onopchenko et al. | 556/479 |

FOREIGN PATENT DOCUMENTS 0337197 3/1989 European Pat. Off.

OTHER PUBLICATIONS

Pergamon Journals, Ltd.; "Catalyzed Hydrosilylation of 2-Methyl 1-Buten-3-Yne with Methyldichlorosilane; Promotional Effect Imparted By the Presence of A Different Chlorosilane." Tetrahedron Letters, vol. 28, No. 32 pp. 3719-3722, 1987.

JCS Dalton; "Organosilicon Chemistry. Part 24: Homogeneous Rhodium-catalysed Hydrosilation of Alkenes and Alkynes: The Role of Oxygen or Hydroperoxides." by Hugh Dickers, R. N. Hazeldine, L. Malkin, A. Mather, R. Parish. pp. 308-313, 1979.

Transition Met. Chem: "Organic Peroxide Assisted Transition Metal Hydrosilylation Catalysis" A. Calhoun, K. Lung, T. Nile, L. Stokes S. Smith pp. 365-368, 1967.

J. American Chem. Soc. 1990, "On the Mechanism of Metal Colloid Catalyzed Hydrosilyation: Proposed Explanations for Electronic Effects and Oxygen Cocatalysis", Larry Lewis. pp. 5998-6004, 1990.

"Hydrosilation Catalyzed by Group VIII Complexes", J. F. Harrod, A. Chalk, pp. 673-684, 1969.

*Primary Examiner*—Paul F. Shaver
*Attorney, Agent, or Firm*—Sharon K. Severance

[57] ABSTRACT

A method for maintaining catalytic activity during a hydrosilylation reaction between a silicon hydride and an unsaturated compound is disclosed. The method comprises reacting a silicon hydride and an unsaturated compound in the presence of a platinum catalyst wherein a peroxide is added into the reaction mixture to maintain the catalytic activity of the platinum catalyst.

18 Claims, No Drawings

METHOD FOR MAINTAINING CATALYTIC ACTIVITY DURING A HYDROSILYLATION REACTION

BACKGROUND OF THE INVENTION

One method known in the art for producing organosilicon compounds comprises reacting a silicon hydride containing compound with an unsaturated compound in the presence of a catalyst. This reaction is commonly referred to as hydrosilylation. Typically the catalyst is platinum metal on a support, a platinum compound generally used in an inert solvent, or a platinum complex, however other catalysts comprising rhodium or nickel may be used. In U.S. Pat. No. 2,823,218 to Speier, et al. a method for the production of organosilicon compounds by reacting an Si—H with a compound containing aliphatic carbon atoms linked by multiple bonds in the presence of a chloroplatinic acid is taught. U.S. Pat. No. 3,220,972 to Lamoreaux teaches a similar process however the catalyst is a reaction product of chloroplatinic acid. In EP Patent Application No. 0337197 to Lewis the catalyst used is a rhodium colloid and the silicon containing reactant must have two to three hydrogen atoms bonded to the silicon.

One of the major problems known in the art with hydrosilylations is the de-activation of the catalyst prior to the completion of the reaction. One method for reactivation of the catalyst has been to expose the reaction mixture to oxygen. For example, U.S. Pat. No. 4,578,497 to Onopchenko, et al. teaches the use of an oxygenated platinum containing catalyst for hydrosilylation with alkylsilanes, $R'R_xSiH_{3-x}$. The oxygenated platinum catalyst is produced by contacting the catalyst with an oxygen-containing gas. In particular, the catalyst is contacted with the oxygen-containing gas by bubbling air into the catalyst mixed with the olefin and with or without an inert solvent under ambient temperatures prior to the reaction. Another technique taught by Onopchenko is to run the hydrosilylation until deactivation occurs, cool to room temperature and then bubble an oxygen-containing gas into the mixture. Following the exposure to oxygen the system is placed under an inert atmosphere and the reaction is again commenced.

The use of peroxides to activate reactions that are otherwise unreactive in the presence of a metallic catalysts has been shown for several reactants and catalysts. In these situations there is no catalytic activity in the absence of the peroxide. Thus, the peroxide is introduced to "start" or activate the reaction rather than to maintain catalytic activity. For example, Licchelli et al., "Catalyzed Hydrosilylation of 2-Methyl-1-buten-3-yne with Methyldichlorosilane; Promotional Effect Imparted by the Presence of a Different Chlorosilane", Tetrahedron Letters, Vol.28,No. 2, pp.3719–3722 (1987) discloses the reaction between 2-methyl-1-butene-3-yne and methyldichlorosilane using chloroplatinic acid and a very small amount of benzoyl-peroxide. In the absence of the peroxide the reaction did not take place.

Dickers et al., "Organosilicon Chemistry. Part 24. Homogeneous Rhodium-catalyzed Hydrosilation of Alkenes and Alkynes: Role of Oxygen or Hydroperoxides", J.C.S. Dalton, pp. 308–313 (1980) discloses the reaction between purified hex-1-ene or hex-yne and triethylsilane in the presence of a rhodium catalyst, [RhCl(PPh$_3$)$_3$], and Bu$^t$OOH. In the absence of Bu$^t$OOH the reaction did not take place. Additionally, Di-t-butyl peroxide did not activate the reaction.

Calhoun et al., "Organic Peroxide Assisted Transition Metal Hydrosilylation Catalysis", Transition Met. Chem., 8, 365–368(1983), discloses peroxides as co-catalysts to increase the catalytic activity of rhodium catalysts. For example Calhoun shows that the yield of the reaction between 1-octene and triethoxysilane was only 4% in the absence of t-BuOOH but increased to 75% when high amount of t-BuOOH was added to the reaction mixture.

It is an object of this invention to provide a method for maintaining catalytic activity during a hydrosilylation reaction wherein the hydrosilylation reaction comprises reacting a silicon hydride having 1 to 3 hydrogen atoms attached to the silicon with unsaturated compounds in the presence of a platinum catalyst and a peroxide.

SUMMARY OF THE INVENTION

The instant invention deals with a method of maintaining catalytic activity in a hydrosilylation reaction wherein the reaction comprises reacting silicon hydrides having 1 to 3 hydrogen atoms attached to the silicon with unsaturated compounds to produce organosilicon compounds. The reaction is catalyzed using a platinum catalyst selected from platinum metal, platinum compounds and platinum complexes. A peroxide is added to maintain the catalytic activity until one or both of the reactants are consumed.

THE INVENTION

This invention is directed to a method of maintaining catalytic activity in a hydrosilylation reaction mixture by introducing a peroxide into the reaction mixture said hydrosilylation reaction comprising, reacting:

(A) a silicon hydride selected from silicon hydrides having the general formulae:

$$R_xSiH_{4-x} \quad \text{(i)}$$
$$R_yH_uSiX_{4-y-u} \quad \text{(ii)}$$
$$R_z(R'O)_{4-z-w}SiH_w \quad \text{(iii)}$$

(iv)

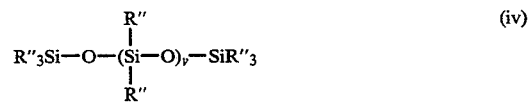
(v)

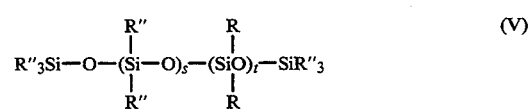
(vi)

and

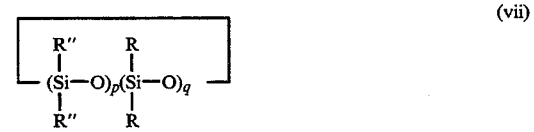
(vii)

wherein each R is independently selected from the group consisting of substituted and unsubstituted alkyl groups having 1 to 30 carbon atoms, substituted and unsubstituted cycloalkyl groups having at least 4 carbon atoms and substituted and unsubstituted aryl groups having 6 to 16 carbon atoms; each R' is independently selected from alkyl groups having 1 to 6 carbon atoms; R" is independently selected from the group consisting of R and the hydrogen atom, with the proviso that at least one R" in each molecule is a hydrogen atom; X is a halide; p has a value of at least one; q has a value of at least 1 with the proviso that p+q has a value of 3 to 8; r has a value of 3 to 8; s has a value of 1 or greater; t has a value of 1 or greater; u has a value of 1, 2, or 3 with the proviso that $u+y \leq 3$; v has a value of zero or an integer of 1 or greater; w has a value of 1 to 3; x has the value of 1 to 3; y has a value of 0 to 2; and z has a value of 0 to 2 with the proviso that $w+z \leq 3$, with (B) unsaturated compounds selected from the group consisting of (i) substituted or unsubstituted unsaturated organic compounds or mixtures thereof, (ii) substituted or unsubstituted unsaturated silicon compounds or mixtures thereof and, (iii) mixtures of (i) and (ii); in the presence of (C) a hydrosilylation catalyst selected from the group consisting of (a) platinum metal on a support, (b) platinum compounds, and (c) platinum complexes; wherein a peroxide is added to the reaction mixture whereby said hydrosilylation reaction is maintained.

As noted above, the silicon hydrides useful in the instant invention may be exemplified by compounds or mixtures of compounds of the formulae:

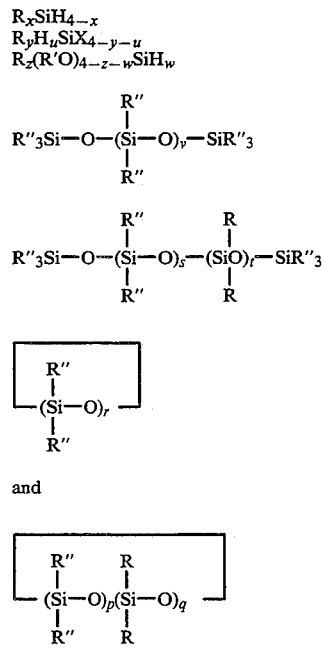

The silicon hydrides useful in the instant invention may be specifically exemplified by, but not limited to, trimethylsilane, dimethylphenylsilane, dimethylsilane, dichlorosilane, dimethoxysilane, methyldimethoxysilane, triethylsilane, triethoxysilane, trichlorosilane, methyldichlorosilane, dimethylchlorosilane, trimethoxysilane, 1,1,1,2,3,3,3-heptamethyltrisiloxane, dimethylsiloxane/methylhydrogensiloxane copolymers, methylhydrogencyclic siloxanes, and others.

The silicon hydride is reacted with unsaturated compounds selected from the group consisting of (i) substituted or unsubstituted unsaturated organic compounds or mixtures thereof, (ii) substituted or unsubstituted unsaturated silicon compounds or mixtures thereof and, (iii) mixtures of (i) and (ii). More specific examples of the unsaturated compounds being unsubstituted cycloalkenyl compounds having at least 4 carbon atoms, substituted cycloalkenyl compounds having at least 4 carbon atoms, linear alkenyl compounds having 2 to 30 carbon atoms, branched alkenyl compounds having 4 to 30 carbon atoms, and mixtures thereof, and the like.

The substituted and unsubstituted cycloalkenyl compounds useful in the instant invention are those olefins that contain one or more unsaturated carbon-carbon bond in the ring. The unsubstituted cycloalkenyl compounds may be further exemplified by, but not limited to, cyclobutene, cyclopentene, cyclohexene, cycloheptene, cyclooctene, cyclopentadiene, 1,3-cyclohexadiene, 1,3,5,7-cycloheptadiene, and cyclooctatetraene. The substituted cycloalkenyl compounds useful in the instant invention are only those that contain substitution on the saturated carbons (i.e. not at the C=C bond). The substituted unsaturated alicyclic compounds useful in the instant invention may be further exemplified by, but not limited to 3-methylcyclopentene, 3chlorocyclobutene, 4-phenyl-cyclohexene and 3methylcyclopentadiene. The preferred cycloalkenyl compounds are cyclohexene and cyclopentene.

The unsaturated cycloalkenyl compounds useful in the instant invention are commercially available. Prior to the reaction of the unsaturated cycloalkenyl compound it may be preferable to treat or purify the unsaturated cycloalkenyl compound. Methods which can be used for treating or purifying the unsaturated cycloalkenyl compound are those methods known in the art and include but are not limited to distillation, treatment with alumina and others.

Other compounds that are useful in this invention are unsaturated linear and branched alkyl compounds which include, but are not limited to those compounds with terminal unsaturation such as 1-hexene, and those compounds with internal unsaturation such as trans-2-hexene; and unsaturated aryl containing compounds such as styrene and α-methylstyrene.

Other unsaturated compounds useful in the instant invention include olefinically unsaturated functional alkenyl compounds which contain halogen, oxygen in the form of acids, anhydrides, alcohols, esters, and ethers, and nitrogen.

The halogenated olefinically unsaturated functional alkenyl compounds which may be used herein may be exemplified by compounds such as vinyl chloride, allyl chloride, allyl bromide, allyl iodide, allylene bromide, methallyl chloride, tri- and tetra- chloroethylene, tetrafluoroethylene, chloroprene, vinylidene chloride, and dichlorostyrene.

Suitable oxygen containing olefinically unsaturated functional alkenyl compounds may be exemplified by ethers such as the allyl and vinyl ethers, alcohols such as allyl alcohol (vinyl carbinol), methylvinylcarbinol and ethynyldimethyl-carbinol, acids such as acrylic, methacrylic, vinylacetic, oleic, sorbic, and linolenic, and esters such as vinyl acetate, allyl acetate, butenyl acetate, allyl stearate, methylacrylate, ethylcrotonate, diallyl succinate and diallyl phthalate. Suitable nitrogen containing olefinically unsaturated functional alkenyl compounds may be exemplified by indigo, indole, acrylonitrile, and allyl cyanide.

Specifically included within the definition of olefinic unsaturated groups are those olefinic unsaturated groups that are substituted by organofunctional moieties such as

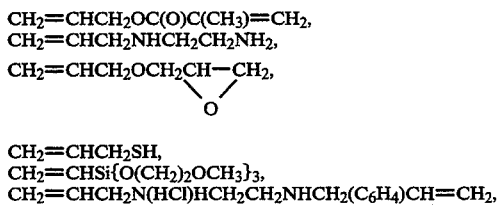

CH₂=CHCH₂SH,
CH₂=CHSi{O(CH₂)₂OCH₃}₃,
CH₂=CHCH₂N(HCl)HCH₂CH₂NHCH₂(C₆H₄)CH=CH₂, and the like.

Unsaturated silicon compounds that are useful in this invention are for example $(CH_2=CH)_aSi(OR')_{3-a}$ wherein R' has the same meaning as that set forth above and a has a value of 1 or 2, CH₂=CHCH₂Si(OR')₃ and CH₂=CHCH₂Si(CH₃)(OR')₂, and the like.

The unsaturated compounds useful in the instant invention are commercially available. Prior to the reaction of the unsaturated compound it may be preferable to treat or purify the unsaturated compound. Methods which can be used for treating or purifying the unsaturated compound are those methods known in the art and include but are not limited to distillation, treatment with alumina and others.

The relative amounts of silicon hydride and unsaturated compound employed in the process herein have no technical limitations. One unsaturated linkage, for example, ethylene, is obviously the stoichiometric requirement per silicon bonded hydrogen atom. However there is no absolute necessity for equivalent amounts of the reactants to be employed and any desired excess of either reactant can be present. In fact an excess of one reactant, typically the unsaturated compound, may often be desirable to force the reaction to completion or to make the greatest use of the reactant which is the most expensive or most rare. Thus the choice of reactant ratios is mostly a matter of practicality and economics based upon the reactants employed. It is preferred to use a reactant ratio ranging from 1:20 to 20:1 in terms of equivalents of Si—H compound to unsaturated compound, the more usual operating range being in the region of from 1:2 to 2:1.

In some cases it may be desirable to employ also a solvent for one or both of the reactants. The amount of solvent employed is not critical and can vary without limit except for economic considerations. Any solvent can be employed which will dissolve but be inert toward the desired reactants under the conditions of the reaction and which will not interfere with the reaction. The solvent should also be selected so that easy separation of the products after the reaction can be enhanced.

The reaction between the silicon hydride and unsaturated compound is catalyzed using a hydrosilylation catalyst. Hydrosilylation catalysts useful in the instant invention may be exemplified by, but not limited to platinum metal, platinum compounds, and platinum complexes. The platinum compounds and platinum complexes may be exemplified by chloroplatinic acid, chloroplatinic acid hexahydrate, Karstedt's catalyst (Pt #2, Pt(ViMe₂SiOSiViMe₂)₂), dichloro-bis(triphenylphosphine)platinum (II), cis-dichloro-bis(acetonitrile)-platinum(II), dicarbonyldichloroplatinum(II), platinum chloride, platinum oxide and others. The platinum metal can be deposited on a support such as charcoal, alumina, zirconia, carbon, silica gel, nylon, polyacrylonitrile, and others. Any platinum containing material which effects the reaction between the silicon hydride and the unsaturated portion of the unsaturated compound is useful in the instant invention.

Suitable amounts of the platinum containing compounds and the platinum complexes vary within wide limits. Concentrations on the order of 1 mole of catalyst (providing one mole of platinum) per billion moles of unsaturated groups in the unsaturated compound may be useful. Concentrations as high as 1 to 10 moles of catalyst per thousand moles of unsaturated groups in the unsaturated compound may also be employed. Generally the economics of the reaction dictates the particular level of catalyst employed. Preferable concentrations are from 1 mole of platinum per 1,000 moles of unsaturated groups to 1 mole of platinum per 1,000,000 mole of unsaturated groups in the unsaturated compound. Suitable amounts of supported platinum include, for example, from at least about 0.1 weight percent preferably 0.1 to about 10 weight percent, more preferably from about 0.5 to 5 weight percent based upon elemental platinum. A further description of platinum catalysts useful in the instant invention is found in, but not limited to, U.S. Pat. Nos. 4,578,497, 3,775,452, 3,220,972 and 2,823,218, herein incorporated by reference for what they teach about platinum catalysts per se.

The catalyst may be dissolved in a solvent for ease of handling and to facilitate measuring the minute amounts needed. Preferably the solvent should be inert. Suitable solvents include the various hydrocarbon solvents such as benzene, toluene, xylene, and mineral spirits and polar solvents such as alcohols, various glycols and esters.

In the instant invention, the reaction is carried out in the continuous presence of a peroxide. The peroxide, when added during the course of the reaction, provides a means for maintaining the catalytic activity during the reaction. Peroxides useful in the instant invention may be exemplified by, but not limited to, organic peroxides and hydroperoxides such as t-butyl hydroperoxide, t-amyl hydroperoxide, di-t-butyl peroxide and others; diacyl peroxides such as dibenzoyl peroxide, diacetyl peroxide and others; and other peroxides and hydroperoxides.

The amount of peroxide which must be added will be dependent on the operating conditions, the reactants and the amount of catalyst present. Typically 0.05 to 10 weight parts peroxide per 100 weight parts of reactants can be used, preferably 0.1 to 1 weight parts peroxide per 100 weight parts of reactants. The peroxides are typically admixed with the reactants prior to introduction into the reaction vessel, however, the peroxide may be added separately to the reaction vessel from the reactants.

The reaction temperature can vary over an extremely wide range. The temperature will affect the life of the peroxide therefore it is dependant on the type of peroxide being employed. The optimum temperature depends upon the concentration of catalyst present, concentration of peroxide and the nature of the reactants. Best results are obtained by initiating the reaction at about 20° to 250° C. and maintaining the reaction within reasonable limits of this range. The reaction is typically exothermic and the reaction temperature can be maintained by controlling the rate of addition of one of the reactants or applying cooling means to the reaction vessel. It is preferred although not necessary, when operating at atmospheric pressure, to use an operating temperature such that the reaction is carried out under reflux conditions.

The reaction can be carried out at atmospheric, subatmospheric, or superatmospheric pressures. The choice of conditions is largely a matter of choice based on the nature of the reactants and the equipment available. Non-volatile reactants are especially adaptable to being heated at atmospheric pressure. It may be preferred under certain conditions to run the reaction at pressures above atmospheric to reduce the volatility of the reactants at higher temperatures.

The amount of time for the reaction to go to completion depends upon the reactants, reaction temperature, catalyst concentration, and peroxide concentration. Determination of when the reaction has gone to completion can be accomplished by simple analytical methods such as gas liquid chromatography or by infrared spectrometry.

The reaction may be run on a continuous, semi-continuous, or batch reactor. A continuous reactor comprises a means wherein the reactants are introduced and products are withdrawn simultaneously. The continuous reactor may be a tank, a tubular structure, a tower, or some other like structure, the overall design not being essential. A semi-continuous reactor comprises a means wherein some of the reactants or a reaction heel are charged at the beginning and the remaining reactants are fed continuously as the reaction progresses. The product may optionally be simultaneously be withdrawn from the semi-continuous reactor. A batch reactor comprises a means wherein all the reactants are added at the beginning and processing is carried out according to a predetermined course of reaction during which no reactant is fed into or removed from the reactor. Typically a batch reactor will be a tank with or without agitation means.

So that those skilled in the art can understand and appreciate the invention taught herein, the following examples are presented, it being understood that these examples should not be used to limit the scope of this invention found in the claims attached hereto.

EXAMPLE 1

A mixture of 37,959 grams (330 moles) of $MeHSiCl_2$ and 20,199 grams (264 moles) of allyl chloride was pressurized to 10 psi with nitrogen and was pumped at a rate of approximately 1570 grams/hour at a pressure of 300 to 350 psi into 160 grams of 1% Pt/4–8 mesh carbon contained in a 1×27 stainless steel pipe heated to 100° C. in boiling water. At the start of the run the hottest part of the catalyst bed ranged from 190° to 210° C. Approximately half way through the run the temperature decreased to 170° C. and by the end of the run the temperature had decreased to 154° to 163° C. The change in the temperature of the catalyst bed was very gradual. Benzoyl peroxide ($BzO_2$), 1 gram per 1,000 gram mixed reactants, was added during the first 18.34 hours of the run. The concentration of benzoyl peroxide was increase to 2 gram per 1,000 gram of mixed reactants for the next 4.85 hours. Di-t-butyl peroxide (DBP), 2 grams per 1,000 grams mixed reactants was then added for the next 2.17 hours. The use of peroxide was then discontinued for the remaining 11.64 hours of the run. Table 1 shows the composition of the reaction product at the various times during the run. A total of 41.25 grams (0.16) moles of benzoyl peroxide and 5.28 g (0.36 mole) di-t-butyl peroxide were employed. At the end of the experiment $2.4 \times 10^{-5}$ moles of platinum per mole of silane had been utilized.

TABLE 1

| Time (hrs) | Peroxide Used | V.P.C. Area % Composition | | | | |
|---|---|---|---|---|---|---|
| | | Propylene | $MeSiHCl_2$ and Allyl Chloride | $MeSiCl_3$ | $PrMeSiCl_2$ | $Cl(CH_2)_3SiMeCl_2$ |
| 18.3 | $BzO_2$ (0.1%) | 0.93 | 2.91 | 18.36 | 19.43 | 58.7 |
| 4.9 | $BzO_2$ (0.2%) | 1.1 | 6.7 | 17.6 | 17.2 | 57.5 |
| 2.2 | DBP (0.2%) | 1.7 | 7.25 | 17.9 | 16.15 | 56.95 |
| 11.6 | none | 1.5 | 15.0 | 17.3 | 14.6 | 51.5 |

Comparative Example 1

A mixture of 14,050 grams (122 moles) of $MeHSiCl_2$ and 6,555 grams (85.6 moles) of allyl chloride was pressurized to 10 psi with nitrogen and pumped at 300 psi into 1% Pt/4–8 mesh carbon contained in a 1×27 stainless steel pipe heated to 80° C. in boiling water. The system ran well for the first 10 hours at a reactant flow rate of 600 to 1100 g/hour producing a crude product which contained 53 area % chloropropylmethyldichlorosilane. During the next 2 hours at flow rates of 600 to 800 g/hr the catalyst deactivated resulting in a crude product containing less than 20 area % chloropropylmethyldichlorosilane. Analysis of the catalyst by emission spectroscopy showed 0.5% Pt in the deactivated catalyst. The deactivated catalyst was removed and replaced with 146 grams of fresh 1% Pt/C. The remainder of the column was filled with porcelain saddles to prevent agitation of the catalyst granules. The fresh catalyst was wet with 140 ml. of crude $ClCH_2CH_2CH_2SiMeCl_2$.

A mixture of 10,825 grams (94.2 moles) of $MeHSiCl_2$ and 5,400 grams (70.6 moles) of allyl chloride was added to the unused reactants. The combined mixture was pressurized to 10 psi with nitrogen and pumped at 300 psi into the 146 grams of 1% Pt/4–8 mesh carbon catalyst contained in the 1×27 stainless steel pipe heated to 90° C. in boiling water. The reaction was exothermic and further heating was not necessary to maintain the water bath at 90° to 95° C. The system was run for a total of 23 hours over a period of 5 days. During the first 10 hours the system was operated a feed rates up to 1600 g/hr. of mixed reactants obtaining a crude which contained 52 to 60 area % chloropropylmethyldichlorosilane. After 13 hours of operation the feed rate had to be slowly reduced to 440 g/hr. to maintain greater than 50 area % chloropropylmethyldichlorosilane showing that loss of catalyst activity was occurring. A product quantity of 22,154 grams was obtained while only 60 ml of material was collected in the cold trap. Analysis of the catalyst by emission spectroscopy showed 0.47% Pt.

What is claimed is:

1. A method of maintaining catalytic activity during a hydrosilylation reaction by adding a peroxide into the hydrosilylation reaction wherein the hydrosilylation reaction comprises, reacting:

(A) a silicon hydride selected from silicon hydrides having the general formulae:

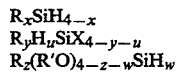  (i)
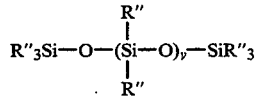  (ii)
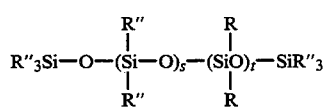  (iii)

  (iv)

$$R''_3Si-O-(Si(R'')-O)_v-SiR''_3$$

$$R''_3Si-O-(Si(R'')-O)_s-(Si(R)O)_t-SiR''_3 \quad (V)$$

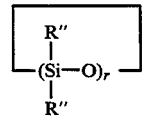  (vi)

and

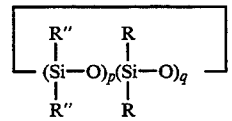  (vii)

wherein each R is independently selected from the group consisting of substituted and unsubstituted alkyl groups having 1 to 30 carbon atoms, substituted and unsubstituted cycloalkyl groups having at least 4 carbon atoms and substituted and unsubstituted aryl groups having 6 to 16 carbon atoms; each R' is independently selected from alkyl groups having 1 to 6 carbon atoms; R'' is independently selected from the group consisting of R and the hydrogen atom, with the proviso that at least one R'' in each molecule is a hydrogen atom; X is a halide; p has a value of at least one; q has a value of at least 1 with the proviso that p+q has a value of 3 to 8; r has a value of 3 to 8; s has a value of 1 or greater; t has a value of 1 or greater; u has a value of 1, 2, or 3 with the proviso that u+y≦3; v has a value of zero or an integer of 1 or greater; w has a value of 1 to 3; x has the value of 1 to 3; y has a value of 0 to 2; and z has a value of 0 to 2 with the proviso that w+z≦3, with (B) unsaturated compounds selected from the group consisting of
  (i) substituted or unsubstituted unsaturated organic compounds or mixtures thereof,
  (ii) substituted or unsubstituted unsaturated silicon compounds or mixtures thereof and,
  (iii) mixtures of (i) and (ii); in the presence of
(C) a hydrosilylation catalyst selected from the group consisting of (a) platinum metal on a support, (b) platinum compounds, and (c) platinum complexes; wherein a peroxide is added to the reaction mixture whereby said hydrosilylation reaction is maintained.

2. A method as claimed in claim 1 wherein the hydrosilylation catalyst is platinum metal on support.

3. A method as claimed in claim 2 wherein the support is charcoal.

4. A method as claimed in claim 1 wherein the silicon hydride has the formula $$R_yH_uSiX_{4-y-u} \quad (ii)$$

wherein each R is independently selected from the group consisting of substituted and unsubstituted alkyl groups having 1 to 30 carbon atoms, substituted and unsubstituted cycloalkyl groups having at least 4 carbon atoms and substituted and unsubstituted aryl groups having 6 to 16 carbon atoms; X is a halide; u has a value of 1, 2, or 3 with the proviso that u+y≦3; and y has a value of 0 to 2.

5. A method as claimed in claim 4 wherein the silicon hydride is methyldichlorosilane.

6. A method as claimed in claim 1 wherein the unsaturated compound is a halogenated olefinically unsaturated alkenyl compound.

7. A method as claimed in claim 6 wherein the unsaturated compound is allyl chloride.

8. A method as claimed in claim 1 wherein the peroxide is benzoyl peroxide.

9. A method as claimed in claim 1 wherein the peroxide is di-t-butyl peroxide.

10. A method of maintaining catalytic activity during a hydrosilylation reaction by adding a peroxide into the hydrosilylation reaction wherein the hydrosilylation reaction comprises, reacting:

(A) a silicon hydride selected from silicon hydrides having the general formulae:

$$R_yH_uSiX_{4-y-u} \quad (i)$$

wherein each R is independently selected from the group consisting of substituted and unsubstituted alkyl groups having 1 to 30 carbon atoms, substituted and unsubstituted cycloalkyl groups having at least 4 carbon atoms and substituted and unsubstituted aryl groups having 6 to 16 carbon atoms; X is a halide; u has a value of 1, 2, or 3 with the proviso that u+y≦3; and y has a value of 0 to 2

(B) a halogenated olefinically unsaturated alkenyl compound; in the presence of
(C) a hydrosilylation catalyst selected from the group consisting of platinum metal on a support; wherein a peroxide is added to the reaction mixture whereby said hydrosilylation reaction is maintained.

11. A method as claimed in claim 10 wherein the support is charcoal.

12. A method as claimed in claim 10 wherein the silicon hydride is methyldichlorosilane.

13. A method as claimed in claim 10 wherein the unsaturated compound is allyl chloride.

14. A method as claimed in claim 10 wherein the peroxide is benzoyl peroxide.

15. A method as claimed in claim 10 wherein the peroxide is di-t-butyl peroxide.

16. A method of maintaining catalytic activity during a hydrosilylation reaction by adding a peroxide into the hydrosilylation reaction wherein the hydrosilylation reaction comprises, reacting:

(A) methyldichlorosilane; and
(B) allyl chloride; in the presence of (C) a hydrosilylation catalyst selected from the group consisting of platinum metal on charcoal; wherein a peroxide is added to the reaction mixture whereby said hydrosilylation reaction is maintained.

17. A method as claimed in claim 16 wherein the peroxide is benzoyl peroxide.

18. A method as claimed in claim 16 wherein the peroxide is di-t-butyl peroxide.

* * * * *